United States Patent
Fei et al.

(10) Patent No.: US 10,149,804 B2
(45) Date of Patent: *Dec. 11, 2018

(54) ORAL CARE COMPOSITIONS FOR TOOTH WHITENING

(71) Applicant: Colgate-Palmolive Company, New York, NY (US)

(72) Inventors: Lin Fei, Kendall Park, NJ (US); Prakasarao Mandadi, Flemington, NJ (US); Suman Chopra, Monroe, NJ (US); Michael Prencipe, West Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/636,682

(22) Filed: Jun. 29, 2017

(65) Prior Publication Data

US 2017/0296447 A1 Oct. 19, 2017

Related U.S. Application Data

(63) Continuation of application No. 14/651,143, filed as application No. PCT/US2012/069849 on Dec. 14, 2012, now Pat. No. 9,724,280.

(51) Int. Cl.
  *A61K 8/25* (2006.01)
  *A61K 8/22* (2006.01)
  *A61K 8/81* (2006.01)
  *A61Q 11/00* (2006.01)

(52) U.S. Cl.
  CPC ............... *A61K 8/25* (2013.01); *A61K 8/22* (2013.01); *A61K 8/8176* (2013.01); *A61Q 11/00* (2013.01); *A61K 2800/48* (2013.01)

(58) Field of Classification Search
  CPC ........................................................ A61J 8/25
  USPC ............................................................ 424/53
  See application file for complete search history.

(56) References Cited

U.S. PATENT DOCUMENTS

| 5,776,435 A | 7/1998 | Gaffar et al. |
| 9,155,688 B2 | 10/2015 | Boyd ............... A61Q 11/00 |
| 9,174,070 B2 | 11/2015 | Chopra ............ A61K 8/22 |
| 2005/0036956 A1 | 2/2005 | Fei et al. |
| 2006/0062744 A1 | 3/2006 | Lokken |
| 2007/0071695 A1* | 3/2007 | Chopra ............ A61K 8/20 424/53 |
| 2010/0135921 A1* | 6/2010 | Hughes ............ A61K 8/25 424/49 |
| 2011/0189637 A1 | 8/2011 | Anderson |
| 2012/0058059 A1* | 3/2012 | Chopra ............ A61K 8/20 424/53 |
| 2012/0282192 A1 | 11/2012 | Miller et al. |
| 2013/0287710 A1 | 10/2013 | Chopra et al. |
| 2015/0320669 A1 | 11/2015 | Fei et al. |

FOREIGN PATENT DOCUMENTS

| EP | 1738802 | 1/2007 |
| WO | WO 04/103303 | 12/2004 |
| WO | WO 08/014096 | 1/2008 |
| WO | WO 12/102750 | 8/2012 |

OTHER PUBLICATIONS

Gun'Ko et al., 2004, "Interaction of poly(vinyl pyrrolidone) with fumed silica in dry and wet powders and aqueous suspensions" Colloids and Surfaces A: Physiochemical and Engineering Aspects 233:36-78.
International Search Report and Written Opinion in International Application No. PCT/US2012/069849, dated Nov. 20, 2013.
International Specialty Products, Inc., 2004, "Peroxydone XL-10C Tentative Sales Specifications," www.ispcorp.com.
International Specialty Products, Inc., 2009, "Product Sales Specifications Peroxydone XL-10F," www.ispcorp.com.
ISP Technologies, Inc., 2011, "Polyplasdone XL-10 Certificate of Analysis," www.ispcorp.com.
Written Opinion in International Application No. PCT/US2012/069849, dated Feb. 5, 2015.

\* cited by examiner

*Primary Examiner* — Walter E Webb

(57) ABSTRACT

Described herein are oral care compositions comprising a thickening system comprising a first thickening agent and a second thickening agent, wherein the first thickening agent comprises greater than 15 wt % of the mixture of the first and second thickening agents in the thickening system.

12 Claims, No Drawings

ORAL CARE COMPOSITIONS FOR TOOTH WHITENING

BACKGROUND

Formula modifications made to stabilize single phase peroxide containing compositions may result in compositions which are difficult to pump during the manufacturing process. There is thus a need for improved single phase peroxide containing compositions, for example dentifrice compositions, which not only exhibit cosmetic stability of the peroxide, and so are stable for long-term storage and are suitable for everyday consumer use, but also have rheological properties which make them easy to pump during manufacture and packaging.

SUMMARY

In some embodiments, the present invention provides an oral care composition comprising (i) a whitening complex comprising crosslinked polyvinylpyrrolidone complexed with hydrogen peroxide, and (ii) a thickening system comprising a first thickening agent comprising a silica; and a second thickening agent comprising crosslinked polyvinylpyrrolidone. In some embodiments, the first thickening agent comprises greater than 15 wt % of the weight of the mixture of the first and second thickening agents in the thickening system.

In some embodiments, the present invention provides methods for whitening teeth comprising administering anyone of the compositions described herein to the oral cavity of a subject in need thereof.

Optionally, the first thickening agent comprises at least one silica selected from the group consisting of fumed silica and colloidal silica. Optionally, the first thickening agent comprises or consists of fumed silica.

Optionally, the first thickening agent comprises from about 40 to about 80 wt % of the weight of the mixture of the first thickening agent and second thickening agent in the thickening system.

Optionally, the first thickening agent comprises a silica in an amount of from about 0.5 wt % to about 6 wt % based on the weight of the composition, further optionally from 1 wt % to 5.5 wt % based on the weight of the composition, further optionally from 2 wt % to 5 wt % based on the weight of the composition, and further optionally from 2.5 wt % to 4.5 wt % based on the weight of the composition.

Optionally, the second thickening agent comprises crosslinked polyvinylpyrrolidone in an amount of from 1 wt % to 5 wt % based on the weight of the composition.

Optionally, the first thickening agent comprises silica in an amount of from 2.5 wt % to 4.5 wt % based on the weight of the composition, the second thickening agent comprises crosslinked polyvinylpyrrolidone in an amount of from 1 wt % to 3.5 wt % based on the weight of the composition, and the total weight of the silica first thickening agent and the crosslinked polyvinylpyrrolidone second thickening agent is from 4.5 wt to 6.5 wt % based on the weight of the composition.

Further optionally, the first thickening agent comprises silica in an amount of from 2.5 wt % to 4.5 wt % based on the weight of the composition, the second thickening agent comprises crosslinked polyvinylpyrrolidone in an amount of from 1.5 wt % to 3 wt % based on the weight of the composition, and the total weight of the silica first thickening agent and the crosslinked polyvinylpyrrolidone second thickening agent is from 5 wt % to 6 wt % based on the weight of the composition.

Optionally, the composition further comprises an ethylene oxide, propylene oxide co-polymer of average molecular weight greater than 5000 Da, being substantially free of an ethylene oxide, propylene oxide co-polymer of average molecular weight less than 5000 Da.

Further optionally, the ethylene oxide, propylene oxide co-polymer comprises (ethylene oxide)$_x$-(propylene oxide)$_y$, wherein x is an integer of 80-150 and y is an integer 30-80.

Optionally, the ethylene oxide, propylene oxide co-polymer is present in an amount of from 5 wt % to 10 wt % based on the weight of the composition.

Optionally, the crosslinked polyvinylpyrrolidone complexed with hydrogen peroxide is present in an amount of from 3 wt % to 17 wt % based on the weight of the composition. Further optionally, the crosslinked polyvinylpyrrolidone complexed with hydrogen peroxide is present in an amount of from 5.5 wt % to 16.5 wt % based on the weight of the composition.

Optionally, the total amount of hydrogen peroxide is from 0.1 wt % to 5 wt % based on the weight of the composition.

Optionally, the composition further comprises polyethylene glycol of average molecular weight 400 to 800 Da. Further optionally, the polyethylene glycol is present in an amount of from 5 wt % to 15 wt % based on the weight of the composition.

Optionally, the composition contains less than 3 wt % water based on the weight of the composition.

Optionally, the composition is a toothpaste comprising a calcium pyrophosphate abrasive. Further optionally, the calcium pyrophosphate is present in an amount of from 5 wt % to 35 wt % based on the weight of the composition. Further optionally, the calcium pyrophosphate is present in an amount of from 8 wt % to 20 wt % based on the weight of the composition.

Optionally, the composition further comprises propylene glycol in an amount of from 10 wt % to 20 wt % based on the weight of the composition.

Optionally, the composition further comprises glycerin in an amount of from 25 wt % to 40 wt % based on the weight of the composition.

Optionally, the composition comprises the following ingredients by weight, each being based on the weight of the composition:

| | |
|---|---|
| Fumed and/or colloidal silica | 2.5-5% |
| Crosslinked polyvinylpyrrolidone | 2.5-5% |
| Glycerin | 30-35% |
| Propylene glycol | 12-18% |
| Ethylene oxide, propylene oxide co-polymer, avg. MW > 5 kDa | 5-10% |
| Polyethylene glycol 600 | 5-15% |
| Crosslinked polyvinylpyrrolidone complexed with 15-25% $H_2O_2$ | 3-8% |
| Calcium pyrophosphate | 10-20%. |

Further optionally, the composition comprises the following ingredients by weight, each being based on the weight of the composition:

| | |
|---|---|
| Fumed and/or colloidal silica | 2.5-4.5% |
| Crosslinked polyvinylpyrrolidone | 1.5-3% |
| Glycerin | 30-35% |
| Propylene glycol | 12-18% |

| | |
|---|---|
| Ethylene oxide, propylene oxide co-polymer, avg., MW > 5 kDa | 5-10% |
| Polyethylene glycol 600 | 5-15% |
| Crosslinked polyvinylpyrrolidone complexed with 15-25% $H_2O_2$ | 3-8% |
| Calcium pyrophosphate | 10-20% | wherein the total amount of ingredients a and b is from 4.5 wt % to 6.5 wt % based on the weight of the composition.

Yet further optionally, the total amount of ingredients a and b is from 5 wt % to 6 wt % based on the weight of the composition.

In the preferred embodiments of the invention, the oral care compositions are stable during long term storage and remain effective to clean and whiten teeth, and in addition the oral care compositions have rheological properties which render them readily pumpable under typical processing conditions encountered during commercial manufacture, with good cosmetic stability during manufacture and use of the compositions.

The invention also provides a method of tooth whitening comprising applying the composition of the invention to the surface of a mammalian tooth.

Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

In some embodiments, the present invention provides an oral care composition comprising (i) a whitening complex comprising crosslinked polyvinylpyrrolidone complexed with hydrogen peroxide, and (ii) a thickening system comprising a mixture of silica as a first thickening agent and crosslinked polyvinvlpyrrolidone as a second thickening agent, the silica comprising greater than 15 wt % of the weight of the mixture of the first and second thickening agents in the thickening system. In some embodiments, the silica comprises greater than 35 wt % of the weight of the mixture of the first and second thickening agents in the thickening system.

In some embodiments, the invention provides a toothpaste comprising an abrasive, e.g., a calcium abrasive. In other embodiments, the invention provides an abrasive-free gel.

In some embodiments, the first thickening agent comprises at least one silica selected from the group consisting of fumed silica and colloidal silica. In some embodiments, the first thickening agent comprises or consists of fumed silica.

In some embodiments, the first thickening agent comprises a silica in an amount of from 40 to 80 wt % of the weight of the mixture of the first and second thickening agents in the thickening system.

In some embodiments, the first thickening agent comprises a silica in an amount of from 2 wt % to 6 wt % based on the weight of the composition, for example from 2.5 wt % to 5 wt % based on the weight of the composition.

In some embodiments, the second thickening agent comprises crosslinked polyvinvlpyrrolidone in an amount of from 1 wt % to 5 wt % based on the weight of the composition. In some embodiments, the crosslinked polyvinvlpyrrolidone has a nitrogen content of less than 13%. In some embodiments, the crosslinked polyvinvlpyrrolidone has a pH less than 8. In some embodiments, the crosslinked polyvinvlpyrrolidone has a pH of about 6. In some embodiments, the crosslinked polyvinvlpyrrolidone comprises particles, wherein the particle size of at least 95% of the particles is less than 75 microns In some embodiments, the first thickening agent comprises a silica in an amount of from 2.5 wt % to 4.5 wt % based on the weight of the composition, second thickening agent comprises the crosslinked polyvinvlpyrrolidone in an amount of from 1 wt % to 3.5 wt % based on the weight of the composition, and the total weight of the first thickening agent and the second thickening agent is from 4.5 wt % to 6.5 wt % based on the weight of the composition.

In some embodiments, the first thickening agent comprises a silica in an amount of from 2.5 wt % to 4.5 wt % based on the weight of the composition, the second thickening agent comprises crosslinked polyvinvlpyrrolidone in an amount of from 1.5 wt % to 3 wt % based on the weight of the composition, and the total weight of the first thickening agent and the second thickening agent is from 5 wt % to 6 wt % based on the weight of the composition.

The compositions of the invention may optionally comprise an additional orally acceptable thickening agent, selected from one or more of, without limitation, carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

In some embodiments, the composition further comprises polymer thickeners selected from (i) polyethylene glycol, (ii) polyethylene glycol—polypropylene glycol block co-polymers having a molecular weight of at least 5000, and (iii) combinations thereof.

In some embodiments, the composition comprises an ethylene oxide, propylene oxide co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;

In some embodiments, the composition comprises an ethylene oxide, propylene oxide co-polymer of average molecular weight greater than 5000 Da, being substantially free of an ethylene oxide, propylene oxide co-polymer of average molecular weight less than 5000 Da. Optionally, the ethylene oxide, propylene oxide co-polymer is present in an amount of from 5 wt % to 10 wt % based on the weight of the composition. Copolymers of ethylene oxide/propylene oxide are useful, but higher molecular weight, e.g., >5000 Da are preferred, e.g. including PLURACARE® L1220 (available from BASF, Wyandotte, Mich., United States of America).

In some embodiments, the composition further comprises polyethylene glycol of average molecular weight 400 to 800 Da, e.g., about 60 Da. Low or medium molecular weight polyethylene glycol, e.g., PEG 400, PEG 600, PEG 800, PEG 1000 and mixtures thereof are useful in the compositions of some embodiments of the invention.

Further optionally, the polyethylene glycol may be present in an amount of from 5 wt % to 15 wt % based on the weight of the composition.

In some embodiments, the oral care compositions may additionally comprise a stabilizing amount of an additional linear polyvinylpyrrolidone, In some embodiments, the crosslinked polyvinylpyrrolidone complexed with hydrogen peroxide is present in an amount of from 0.5 wt % to 17 wt % based on the weight of the composition. In some embodiments, the crosslinked polyvinylpyrrolidone complexed with hydrogen peroxide is present in an amount of from 3 wt % to 12 wt % based on the weight of the composition. In some embodiments, the crosslinked polyvinylpyrrolidone complexed with hydrogen peroxide is present in an amount of from about 5.5 wt % to about 8 wt % based on the weight of the composition.

In some embodiments, the total amount of hydrogen peroxide is from 0.1 wt % to 5 wt % based on the weight of the composition, e.g., 0.1-3 wt %, e.g. about 0.1, 1 or 2 wt %.

Typically, the whitening complex contains about 15-25%, for example about 17-22% of hydrogen peroxide by weight, and about 7-12% total nitrogen by weight; for example, having substantially the same specifications as Polyplasdone® XL-10, e.g., Polyplasdone® XL-10F, e.g., available from International Specialty Products (Wayne, N.J.).

Some embodiments further comprise an abrasive. Yet further embodiments provide oral care compositions comprising from about 5 to about 35 wt % abrasive based on the weight of the composition. Still further embodiments provide oral care compositions comprising from about 10 to about 20 wt % abrasive based on the weight of the composition.

Where abrasives are present, the average particle size is generally about 0.1 to about 30 microns, for example about 1 to about 20 or about 5 to about 15 microns.

The abrasive may comprise a calcium abrasive, such as a calcium phosphate salt, e.g., calcium pyrophosphate, dicalcium orthophosphate dihydrate, tricalcium phosphate, and/or calcium polymetaphosphate In a typical embodiment, the calcium abrasive comprises calcium pyrophosphate. in another embodiment, the calcium abrasive comprises calcium carbonate.

Optionally, the composition is a toothpaste comprising a calcium pyrophosphate abrasive. Further optionally, the calcium pyrophosphate is present in an amount of from 5 wt % to 35 wt % based on the weight of the composition. In some embodiments the calcium pyrophosphate is present in an amount of from about 10 to about 20 wt %, based on the weight of the composition.

The compositions of the invention may also comprise various dentifrice ingredients to adjust the rheology and feel of the composition such as humectants, surface active agents, or gelling agents, etc.

In some embodiments, the oral care composition comprises a vehicle for the active components. The vehicle may comprise humectants, e.g. selected from glycerin, propylene glycol or a combination thereof.

In some embodiments, the oral care composition comprises from about 20 to about 60 wt % humectant based on the weight of the composition.

In some embodiments, the composition further comprises propylene glycol in an amount of from 10 wt % to 20 wt % based on the weight of the composition.

In some embodiments, the composition further comprises glycerin in an amount of from 25 wt % to 40 wt % based on the weight of the composition.

Typical compositions of the invention have a "low water" content, meaning that a total concentration of water, including any free water and all water contained in any ingredients, is less than about 5%, preferably less than 3%, preferably less than 2% water.

Optionally, the composition contains less than 3 wt % water based on the weight of the composition. In some embodiments, the oral care composition contains less than 2 wt % water, e.g., less than 1 wt % water. In some embodiments, the composition is substantially anhydrous.

It is preferred that the vehicle ingredients in particular provide a dentifrice with a viscosity of about 10,000 CPS to about 700,000 CPS, preferably about 30,000 CPS to about 300,000 CPS.

As recognized by one of skill in the art, the oral compositions of the invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine. In some embodiments, the composition may additionally comprise a surfactant, e.g., sodium lauryl sulfate (SLS).

The compositions of the present invention optionally comprise one or more further active material(s), which is or are operable for the prevention or treatment of a condition or disorder of hard or soft tissue of the oral cavity, the prevention or treatment of a physiological disorder or condition, or to provide a cosmetic benefit.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition.

Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. Typically, the anticalculus agent is present at about 0.1% to about 30 wt % based on the weight of the composition.

The oral composition may include a mixture of different anticalculus agents.

In some embodiments, the composition additionally comprises a tartar control agent, e.g., selected from tetrasodium pyrophosphate (TSPP) and sodium tripolyphosphate (STPP).

In one preferred embodiment, tetrasodium pyrophosphate (TSPP) and sodium tripolyphosphate (STPP) are used. The anticalculus agent comprises TSPP at about 1-2% and STPP at about 7% to about 10%, each based on the weight of the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions, each based on the weight of the composition.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5%, each based on the weight of the composition.

In some embodiments, the compositions of the invention optionally comprise an antimicrobial (e.g., antibacterial) agent, e.g., triclosan. A further illustrative list of useful antibacterial agents is provided in such as those listed in U.S. Pat. No. 5,776,435 to Gaffar et al. One or more antimicrobial agents are optionally present in an antimicrobial effective total amount, typically about 0.05% to about 10%, for example about 0.1% to about 3%, each based on the weight of the composition.

In some embodiments, the compositions of the invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the invention may optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

In some embodiments, the composition comprises the following ingredients by weight, each being based on the weight of the composition:

| | |
|---|---|
| Fumed and/or colloidal silica | 2.5-5% |
| Crosslinked polyvinylpyrrolidone | 2.5-5% |
| Glycerin | 30-35% |
| Propylene glycol | 12-18% |
| Ethylene oxide, propylene oxide co-polymer, avg. MW > 5 kDa | 5-10% |
| Polyethylene glycol 600 | 5-15% |
| Crosslinked polyvinylpyrrolidone complexed with 15-25% $H_2O_2$ | 3-8% |
| Calcium pyrophosphate | 10-20%. |

In some embodiments, the composition comprises the following ingredients by weight, each being based on the weight of the composition:

| | |
|---|---|
| Fumed and/or colloidal silica | 2.5-4.5% |
| Crosslinked polyvinylpyrrolidone | 1.5-3% |
| Glycerin | 30-35% |
| Propylene glycol | 12-18% |
| Ethylene oxide, propylene oxide co-polymer, avg. MW > 5 kDa | 5-10% |
| Polyethylene glycol 600 | 5-15% |
| Crosslinked polyvinylpyrrolidone complexed with 15-25% $H_2O_2$ | 3-8% |
| Calcium pyrophosphate | 10-20% | wherein the total amount of ingredients a and b is from 4.5 wt % to 6.5 wt % based on the weight of the composition.

In some embodiments, the total amount of ingredients a and b is from 5 wt % to 6 wt % based on the weight of the composition.

The compositions may optionally comprise any or all of the following ingredient classes and/or particular ingredients by weight, each being based on the weight of the composition:

| | |
|---|---|
| Humectants 35-60%, e.g. | |
| Glycerin | 30-40%, e.g., about 30-35% |
| Propylene glycol | 10-20%, e.g., about 12-18% |
| Thickeners, e.g. | |
| Fumed and/or colloidal silica | 2-6%, e.g., about 2.5-4.5% |
| Crosslinked polyvinylpyrrolidone | 1-5%, e.g., about 1.5-3% |
| Polymers 10-25%, e.g., | |
| Ethylene oxide, propylene oxide co-polymer, avg. MW > 5 kDa | 5-10%, e.g., about 3-8% |
| Polyethylene glycol 600 | 5-15%, e.g., about 10% |
| Whitener, 3-10%, e.g., | |
| Crosslinked polyvinylpyrrolidone complexed with 15-25% H2O2 | 3-10%, e.g., about 5.5% |
| Abrasive, 5-25%, e.g. | |
| Calcium pyrophosphate | 10-20%, e.g., about 15% |
| Fluoride, 0-1%, e.g. | |
| Sodium monofluorophosphate | 0.5-1%, e.g., about 0.76% |
| Surfactant, e.g., SLS | 0-3% |
| Tartar control agent, e.g. TSPP | 0.5-5%, e.g., about 2% |
| Antioxidant, 0.01-5%, e.g. | |
| BHT | 0.03% |
| Flavorings | 0.1-5% |
| Water | <3% |

Methods are provided to whiten an oral surface in a human or animal subject comprising storing in stable form a composition of the invention, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with particular embodiments of the invention, is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Comparative Examples 1 to 4

A number of dentifrices were prepared according to Comparative Examples 1 to 4. The compositions had the following ingredients as specified in Table 1, in which the amounts are in wt %:

TABLE 1

| Ingredient | Comparative Example 1 | Comparative Example 2 | Comparative Example 3 | Comparative Example 4 |
| --- | --- | --- | --- | --- |
| $PEG_{118}$/$PPG_{66}$ co-polymer (Pluracare L1220F) | 7.5 | 7.5 | 7.5 | 7.5 |
| Glycerin | 33.36 | 33.36 | 33.36 | 33.36 |
| Propylene glycol | 15 | 15 | 16 | 15 |
| PEG 600 | 10 | 10 | 10 | 10 |
| Fumed silica | 0 | 6 | 5 | 1.5 |
| Crosslinked PVP | 6 | 0 | 0 | 4.5 |
| Crosslinked PVP/$H_2O_2$ | 5.5 | 5.5 | 5.5 | 5.5 |
| Calcium pyrophosphate | 15 | 15 | 15 | 15 |
| TSPP | 2 | 2 | 2 | 2 |
| Sucralose | 0.05 | 0.05 | 0.05 | 0.05 |
| Sodium saccharin | 0.6 | 0.6 | 0.6 | 0.6 |
| Sodium monofluorophosphate | 0.76 | 0.76 | 0.76 | 0.76 |
| Sodium lauryl sulfate | 2 | 2 | 2 | 2 |
| BHT | 0.03 | 0.03 | 0.03 | 0.03 |
| 85 wt % syrupy phosphoric acid | 0.2 | 0.2 | 0.2 | 0.2 |
| Mint flavor | 2 | 2 | 2 | 2 |
| Total | 100 | 100 | 100 | 100 |

The dentifrice of Comparative Example 1 comprises a thickening system comprising 6 wt % crosslinked polyvinylpyrrolidone but no fumed silica. The dentifrice of Comparative Example 1 represents compositions which employ polyvinylpyrrolidone, but no finned silica, in a whitening dentifrice additionally comprising crosslinked PVP/$H_2O_2$ as a whitening active together with a substantially anhydrous vehicle comprising $PEG_{118}$/$PPG_{66}$ co-polymer (Pluracare L1220F), glycerin, propylene glycol and PEG 600 together with calcium pyrophosphate and TSPP.

The rheological properties of the dentifrice of Comparative Example 1 were measured to determine the viscosity/shear stress rheology profile. The data from the rheology profile was employed to calculate the pressure required to pump the composition of Comparative Example 1 through a pipe 87 meters long having an internal diameter of 1.00 mm at a flow rate of 1100 $cm^3$/second. This calculation was carried out to simulate production conditions during commercial manufacture of the dentifrice.

The results are shown in Table 2.

TABLE 2

| | Comparative Example 1 | Comparative Example 2 | Comparative Example 3 | Comparative Example 4 |
| --- | --- | --- | --- | --- |
| Pressure (bar) | 20.4 | 27.3 | 11.7 | 25.8 |

Table 2 shows that the calculated pumping pressure for Comparative Example 1 is 20.4 bar. This compares to a desired maximum pumping pressure of less than 18 bar, even more desired 15 bar, in the simulated production conditions. Consequently, it must be concluded that the dentifrice of Comparative Example 1 has poor rheology, and would be difficult to pump during manufacture.

The dentifrices of Comparative Examples 2 and 3 comprised a thickening system comprising 6 wt % or 5 wt % fumed silica but no crosslinked polyvinylpyrrolidone. The composition of Comparative Example 3 has 1 wt % increased propylene glycol to accommodate the decreased thickening system. The dentifrices of Comparative Examples 2 and 3 represent compositions which employ hydrated silica as a thickening agent, but no polyvinyl pyrrolidone, in a whitening dentifrice additionally comprising crosslinked PVP/$H_2O_2$ as a whitening active in a substantially anhydrous vehicle comprising glycerin.

The rheological properties of the dentifrices of Comparative Examples 2 and 3 were measured as for Comparative Example 1 and the results are shown in Table 2.

The dentifrice of Comparative Example 2 had a rather high viscosity when the shear stress is high, as demonstrated by the simulated pumping pressure of 27.3 bar. Consequently, it must be concluded that the dentifrice of Comparative Example 2 has poor rheology, and would be difficult to pump during manufacture.

The dentifrice of Comparative Example 3 had a simulated pumping pressure which was within an acceptable range, at 11.7 bar. However, the composition demonstrated poor cosmetic stability, and may separate into plural phases during a pumping operation. Consequently, it must be concluded that the dentifrice of Comparative Example 3 has poor rheology because of poor cosmetic stability due to potential phase separation.

The dentifrice of Comparative Example 4 comprised a thickening system comprising 1.5 wt % fumed silica and 4:5 wt % crosslinked polyvinvlpyrrolidone.

The rheological properties of the dentifrice of Comparative Example 4 were measured as for Comparative Example 1 and the results are shown in Table 2.

The dentifrice of Comparative Example 4 had a rather high viscosity when the shear stress is high, as demonstrated by the simulated pumping pressure of 25.8 bar. Consequently, it must be concluded that the dentifrice of Comparative Example 4 has poor rheology, and would be difficult to pump during manufacture.

Examples 1 to 3

A number of gel dentifrices were prepared according to Examples 1 to 3 which are examples of the compositions of the invention. The compositions had the following ingredients as specified in Table 3, in which the amounts are in wt %:

TABLE 3

| Ingredient | Example 1 | Example 2 | Example 3 |
|---|---|---|---|
| PEG$_{118}$/PPG$_{66}$ co-polymer (Pluracare L1220F) | 7.5 | 7.5 | 7.5 |
| Glycerin | 33.36 | 33.36 | 33.36 |
| Propylene glycol | 15 | 15 | 16 |
| PEG 600 | 10 | 10 | 10 |
| Fumed silica | 4.5 | 3 | 2.5 |
| Crosslinked PVP | 1.5 | 3 | 2.5 |
| Crosslinked PVP/H$_2$O$_2$ | 5.5 | 5.5 | 5.5 |
| Calcium pyrophosphate | 15 | 15 | 15 |
| TSPP | 2 | 2 | 2 |
| Sucralose | 0.05 | 0.05 | 0.05 |
| Sodium saccharin | 0.6 | 0.6 | 0.6 |
| Sodium monofluorophosphate | 0.76 | 0.76 | 0.76 |
| Sodium lauryl sulfate | 2 | 2 | 2 |
| BHT | 0.03 | 0.03 | 0.03 |
| Phosphoric acid | 0.2 | 0.2 | 0.2 |
| Mint flavor | 7 | 2 | 2 |
| Total | 100 | 100 | 100 |

The dentifrice of Example 1 comprised a thickening system comprising 4.5 wt % fumed silica and 1.5 wt % crosslinked polyvinvipyrrolidone. The remaining ingredients and amounts thereof were the same as for the dentifrice of Comparative Example 1.

The theological properties of the dentifrice of Example 1 were measured as discussed above for the Comparative Examples to determine the viscosity/shear stress rheology profile. The data from the rheology profile was employed to calculate the pressure required to pump the composition of Example 1 through a pipe 87 meters long having an internal diameter of 100 mm at a flow rate of 1100 cm$^3$/second. This calculation was carried out to simulate production conditions during commercial manufacture of the dentifrice.

The results are shown in Table 4.

TABLE 4

| | Example 1 | Example 2 | Example 3 |
|---|---|---|---|
| Pressure (bar) | 13.1 | 17.5 | 13.7 |

Table 4 shows that the calculated pumping pressure for Example 1 was 13.1 bar. This is less than the more desired maximum pumping pressure of 18 bar in the simulated production conditions. Consequently, the dentifrice of Comparative Example 1 has good rheology and can readily he pumped during manufacture.

The dentifrice of Example 2 comprised a thickening system comprising 3 wt % fumed silica and 3 wt % crosslinked polyvinvlpyrrolidone. The remaining ingredients and amounts thereof were the same as for the dentifrice of Example 1, The rheological properties of the dentifrice of Example 2 were measured as discussed above for Example 1 to determine the viscosity/shear stress rheology profile. The data from the rheology profile was again employed to calculate the pressure required to pump the composition of Example 2 as described above for Example 1. Table 4 shows that the calculated pumping pressure for Example 2 was 17.5 bar. This is less than the desired maximum pumping pressure of 18 bar in the simulated production conditions. Consequently, the dentifrice of Example 2 has good rheology and can readily be pumped during manufacture.

The dentifrice of Example 3 comprised a thickening system comprising 2.5 wt % fumed silica and 2.5 wt % crosslinked polyvinvipyrrolidone. The remaining ingredients and amounts thereof were the same as for the dentifrice of Example 1, except that the propylene glycol amount was increased from 15 wt % to 16 wt % since the thickening system comprised 5 wt % of the composition rather than 6 wt % of the composition as for Examples 1 and 2, The rheological properties of the dentifrice of Example 3 were measured as discussed above for Example 1 to determine the viscosity/shear stress rheology profile. The data from the rheology profile was again employed to calculate the pressure required to pump the composition of Example 3 as described above for Example 1. Table 4 shows that the calculated pumping pressure for Example 3 was 13.7 bar. Consequently, the dentifrice of Example 3 has good rheology and can readily be pumped during manufacture.

The data described in the Examples evidences the unexpected improvement in rheology, in particular the ability to be pumped during manufacture while retaining cosmetic stability, of the whitening compositions of the invention.

While particular embodiments of the invention have been illustrated and described, it will be obvious to those skilled in the art that various changes and modifications may be made without departing from the scope of the invention as defined in the appended claims.

The invention claimed is:

1. An oral care composition comprising: (i) a whitening complex comprising crosslinked polyvinylpyrrolidone complexed with hydrogen peroxide, and (ii) a thickening system comprising silica as a first thickening agent; and crosslinked polyvinylpyrrolidone as a second thickening agent, wherein the silica comprises greater than 15 wt % of the weight of the mixture of the silica and the crosslinked polyvinylpyrrolidone in the thickening system and wherein the silica is present in an amount of from 2.5 wt % to 4.5 wt % based on the weight of the composition, the crosslinked polyvinylpyrrolidone is present in an amount of from 1 wt % to 3.5 wt % based on the weight of the composition, and the total weight of the silica and the crosslinked polyvinylpyrrolidone is from 4.5 wt % to 6.5 wt % based on the weight of the composition; wherein:

the silica comprises from 40% wt to 80 wt % of the weight of the mixture of the silica and the crosslinked polyvinylpyrrolidone in the thickening system; and the silica comprises at one silica selected from the group consisting of fumed silica and colloidal silica.

2. The composition of claim 1 wherein the silica is present in an amount of from 2.5 wt % to 4.5 wt % based on the weight of the composition, the crosslinked polyvinylpyrrolidone is present in an amount of from 1.5 wt % to 3 wt % based on the weight of the composition, and the total weight of the silica and the crosslinked polyvinylpyrrolidone is from 5 wt % to 6 wt % based on the weight of the composition.

3. The composition of claim 1 further comprising an ethylene oxide, propylene oxide co-polymer of average molecular weight greater than 5000 Da, being substantially free of an ethylene oxide, propylene oxide co-polymer of average molecular weight less than 5000 Da.

4. The composition of claim 3 wherein the ethylene oxide, propylene oxide co-polymer comprises (ethylene oxide)$_x$-(propylene oxide)$_y$ where x is an integer of 80-150 and y is an integer 30-80.

5. The composition of claim 3 wherein the ethylene oxide, propylene oxide co-polymer is present in an amount of from 5 wt % to 10 wt % based on the weight of the composition, and/or wherein the crosslinked polyvinylpyrrolidone complexed with hydrogen peroxide is present in an amount of from 3 wt % to 17 wt % based on the weight of the composition, and/or wherein the total amount of hydrogen peroxide is from 0.1 wt % to 5 wt % based on the weight of the composition.

6. The composition of claim 1 further comprising polyethylene glycol of average molecular weight 400 to 800 Da, wherein the polyethylene glycol is present in an amount from 5 wt % to 15 wt % based on the weight of the composition.

7. The composition of claim 1 which contains less than 3 wt % water based on the weight of the composition.

8. The composition of claim 1 which is a toothpaste comprising a calcium pyrophosphate abrasive, wherein the calcium pyrophosphate is present in an amount from 5 wt % to 35 wt % based on the weight of the composition.

9. The composition of claim 1 further comprising propylene glycol in an amount from 10 wt % to 20 wt % based on the weight of the composition, and/or wherein the composition further comprises glycerin in an amount from 25 wt % to 40 wt % based on the weight of the composition.

10. A method of tooth whitening comprising applying the composition of claim 1 to the surface of a mammalian tooth.

11. The composition of claim 1 further comprising an antioxidant.

12. The composition of claim 11, wherein the antioxidant comprises butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

* * * * *